United States Patent [19]
Miesel et al.

[11] Patent Number: 6,162,180
[45] Date of Patent: Dec. 19, 2000

[54] NON-INVASIVE CARDIAC MONITORING SYSTEM AND METHOD WITH COMMUNICATIONS INTERFACE

[75] Inventors: Keith A. Miesel, St. Paul; Lee Stylos, Stillwater, both of Minn.

[73] Assignee: Medtronic, Inc., Minneapolis, Minn.

[21] Appl. No.: 09/221,038

[22] Filed: Dec. 28, 1998

[51] Int. Cl.$^7$ .............................. A61B 5/08; A61B 5/02
[52] U.S. Cl. ...................... 600/481; 600/500; 600/529
[58] Field of Search .................... 600/481–486, 600/500–504, 529–534, 538–539

[56] References Cited

U.S. PATENT DOCUMENTS

| | | |
|---|---|---|
| 4,548,209 | 10/1985 | Wielders et al. . |
| 4,556,063 | 12/1985 | Thompson et al. . |
| 4,693,253 | 9/1987 | Adams . |
| 4,750,495 | 6/1988 | Moore et al. . |
| 4,821,723 | 4/1989 | Baker, Jr. et al. . |
| 4,830,006 | 5/1989 | Haluska et al. . |
| 4,903,701 | 2/1990 | Moore et al. . |
| 4,949,724 | 8/1990 | Manhutte et al. ...................... 600/526 |
| 4,979,730 | 12/1990 | Coben et al. . |
| 5,113,859 | 5/1992 | Funke . |
| 5,131,388 | 7/1992 | Pless et al. . |
| 5,144,949 | 9/1992 | olson . |
| 5,154,170 | 10/1992 | Bennett et al. . |
| 5,158,078 | 10/1992 | Bennett et al. . |
| 5,312,453 | 5/1994 | Shelton et al. . |
| 5,341,430 | 8/1994 | Bardy . |
| 5,342,406 | 8/1994 | Thompson . |
| 5,354,316 | 10/1994 | Keimel et al. . |
| 5,447,519 | 9/1995 | Peterson . |
| 5,545,186 | 8/1996 | Olson et al. . |
| 5,619,991 | 4/1997 | Sloane ..................................... 600/300 |
| 5,836,300 | 11/1998 | Mault ...................................... 600/532 |
| 5,971,934 | 10/1999 | Scherer et al. .......................... 128/923 |

*Primary Examiner*—Cary O'Connor
*Assistant Examiner*—Michael Astorino
*Attorney, Agent, or Firm*—Michael B. Atlass; Harold R. Patton

[57] ABSTRACT

A system and method for determining a patient's cardiac output in a non-invasive manner and transmitting cardiac output data to a remote host processor, a communications system, or a local output device is disclosed. A non-invasive cardiac monitoring approach utilizes an implantable medical device coupled to an oxygen sensor. The oxygen sensor provides venous oxygen saturation data to the implantable medical device. An oxygen consumption unit produces oxygen consumption data using air exhaled by a patient. A processing unit calculates a cardiac output result in real-time using the venous oxygen saturation data, the oxygen consumption data, and arterial oxygen saturation data assumed to be about 100% or acquired using a sensor external to the patient. The implantable medical device may transmit the venous oxygen saturation data to the processing unit using electromagnetic signals or acoustic signals. The implantable medical device may be a pacemaker, a pacemaker/cardioverter/defibrillator (PCD), an oxygen sensing device, or an implantable hemodynamic monitor. The processing unit may store the cardiac output data/result for a period of time and/or communicate the cardiac output result to the remote host processor substantially in real-time via a communications interface. The interface may include a modem, a computer interface, a network interface, or a communications system interface, for example. The processing unit may communicate the cardiac output result to the remote host processor in an analog, digital or optical form.

35 Claims, 9 Drawing Sheets

NON-INVASIVE CARDIAC MONITORING SYSTEM AND METHOD WITH COMMUNICATIONS INTERFACE

FIELD OF THE INVENTION

The present invention relates generally to cardiac monitoring systems and methods. More particularly, the present invention pertains to a non-invasive cardiac monitoring system and method provided with a communications interface.

BACKGROUND OF THE INVENTION

Various medical procedures have been developed to assess the cardiac output of a patient. A conventional approach of assessing cardiac output requires an invasive medical procedure by which blood is drawn from the right ventricle of a patient's heart via a catheter apparatus. The drawn blood sample is then analyzed, typically by an off-site laboratory, to determine oxygen saturation of the blood sample. The oxygen saturation data obtained through analysis of the blood sample is combined with other data to compute the patient's cardiac output.

Although conventional techniques for determining a patient's cardiac output are generally accurate, it can be appreciated that the invasive nature of such conventional procedures results in increased costs and involves some degree of risk and discomfort on the part of the patient. Further, such conventional approaches are time consuming, and cannot be employed to provide contemporaneous cardiac output results. Rather, cardiac output results provided using conventional procedures often result in delays on the order of hours or even days. Also, there is a risk to the health care worker associated with the handling and transport of blood samples.

Moreover, conventional cardiac output measurement systems and techniques generally require a patient to travel from home to a physician's office or a health care clinic. It can be appreciated that patients requiring cardiac output monitoring are typically incapacitated to some degree, and traveling to a distant health facility often represents a sizeable undertaking. The inherent inconvenience and discomfort associated with conventional cardiac output monitoring techniques may dissuade patients from participating in needed cardiac output evaluations.

There exists a need for a cardiac output monitoring approach which is non-invasive. There exists a further need for such an approach which may be implemented in a patient's home or at a health care clinic location.

SUMMARY OF THE INVENTION

The present invention is directed to a system and method for determining a patient's cardiac output in a non-invasive manner, and for transmitting cardiac output data to a remote host processor, a communications system, or a local output device.

A non-invasive cardiac monitoring system in accordance with the principles of the present invention utilizes an implantable medical device previously implanted in a human body which is coupled to an oxygen sensor situated in the heart. The oxygen sensor provides venous oxygen saturation data to the implantable medical device. An oxygen consumption unit produces oxygen consumption data using air exhaled by a patient. A processing unit calculates a cardiac output result using the venous oxygen saturation data, the oxygen consumption data, and arterial oxygen saturation data assumed to be about 100% or acquired using a sensor external to the patient.

The processing unit receives the venous oxygen saturation data from the implantable medical device and the oxygen consumption data from the oxygen consumption unit substantially simultaneously, and the processing unit calculates the cardiac output result substantially in real-time. The implantable medical device may transmit the venous oxygen saturation data to the processing unit using electromagnetic signals or acoustic signals. The implantable medical device may be a pacemaker, a pacemaker/cardioverter/defibrillator (PCD), an oxygen sensing device, or an implantable hemodynamic monitor, for example. The processing unit may store the cardiac output data/result for a period of time and/or communicate the cardiac output result to the remote host processor substantially in real-time. The cardiac output result is preferably arrived at through use of Fick's principle.

The oxygen consumption unit includes a breathing apparatus comprising a mask which is securable about the patient's nose and mouth. A sensor assembly is provided to measure oxygen consumption directly or, alternatively, indirectly by measuring a flow rate of exhaled air and oxygen content in ambient air. A pulse oximeter may be affixed to the patient's finger to acquire data for purposes of computing arterial oxygen saturation, which may alternatively be assumed to be about 100%.

The monitoring system may further include an interface to effect communication between the processing unit and a remote host processor. Cardiac output data may be communicated to the remote host processor in real-time or in a batch mode. The communication of cardiac output data between the processing unit and the remote host processor may by initiated in response to an instruction signal produced by the remote host processor or in response to the cardiac output result exceeding a preestablished threshold. Cardiac output data may also be communicated to a local or remote output device, such as a display, printer or charting device via the interface. The interface may include a modem, a computer interface, a network interface, or a communications system interface, for example. The processing unit may communicate the cardiac output result to the remote host processor in an analog, digital or optical form.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
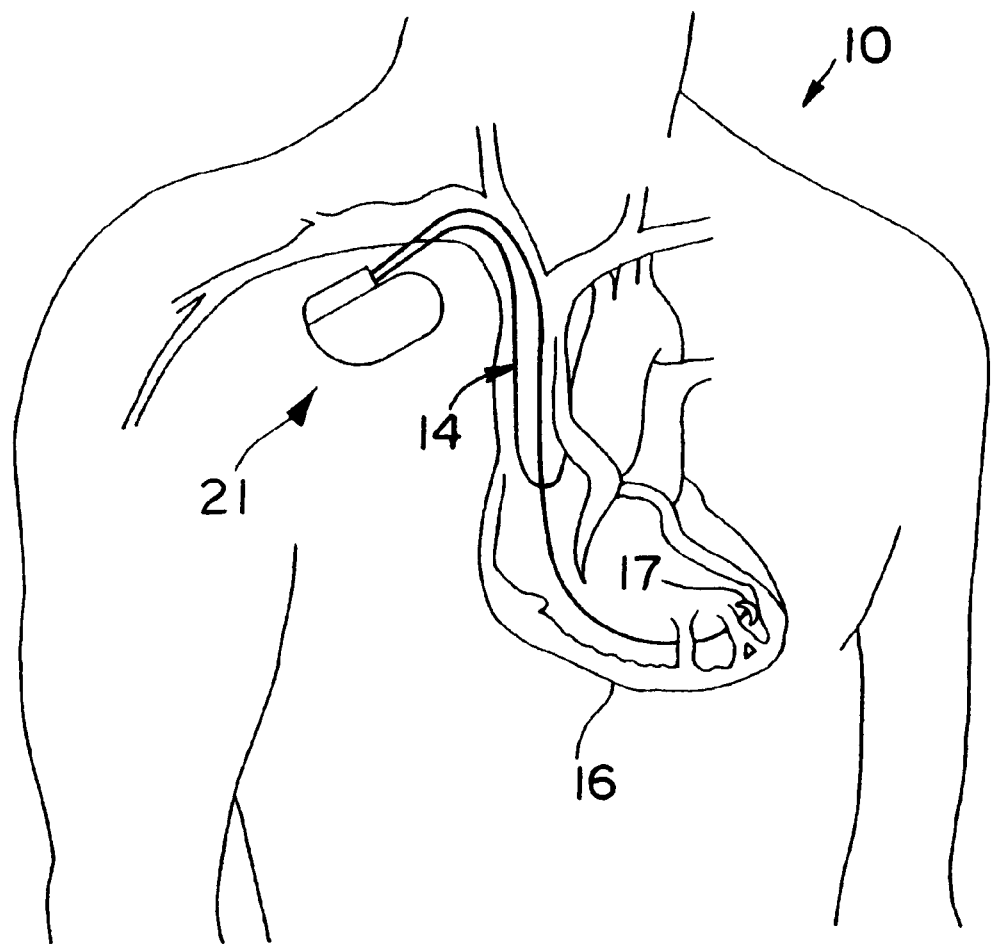
FIG. 1 shows an implantable medical device implanted in a human body and coupled to one or more physiologic sensors for communicating oxygen saturation data, exclusive of or in addition to pressure data, to an external cardiac output processing system in accordance with an embodiment of the present invention.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF THE EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

A non-invasive cardiac monitoring system and method according to the present invention provides for the acquisition and production of cardiac output data utilizing a previously implanted medical device that monitors a patient's heart and a processing unit external to the patient. Venous oxygen saturation data is acquired using a physiologic sensor provided in the heart and coupled to the implantable medical device. Arterial oxygen saturation data may be assumed to be about 100% or, alternatively, acquired using an external physiologic sensor. Oxygen consumption data is acquired through employment of an external breathing apparatus.

Oxygen saturation and consumption data acquired by the implantable medical device is transferred to the external processing unit using electromagnetic or acoustic telemetry techniques. The external processing unit produces cardiac output data using the acquired physiologic data without necessity of performing an invasive procedure on the patient, such as the drawing of blood using a catheter apparatus as is required in accordance with prior art approaches. Cardiac output data may be transmitted to a remote host processor via a communications link and/or displayed or printed using a suitable output device.

A non-invasive cardiac monitoring system according to the present invention is particularly well-suited for use in the patient's home. Cardiac output data acquired from the patient may be transmitted in real-time or non-real time to a remote host processor located at a health care clinic. In accordance with another embodiment, a cardiac monitoring system according to the present invention may be provided in a physician's office to provide for assessment of a patient's cardiac output in real-time.

In accordance with another embodiment of the present invention, hemodynamic status data may be acquired and produced using a non-invasive approach. In accordance with this embodiment, two physiologic sensors provided in a patient's heart and coupled to a medical device implanted in the patient's body cooperate with an external processing unit to acquire and produce hemodynamic status data. The external processing unit produces hemodynamic status data in real-time which may be stored or transmitted to a remote host processor in real-time. A hemodynamic status monitoring system according to the present invention may be configured for home use or use in a health care clinic or physician's office.

Referring now to the drawings, FIG. 1 is a simplified view of a medical device 21 implanted in a human body 10. A single or multiple physiologic sensor assembly 17 is shown implanted in a human heart 16 and coupled to the medical device 21. The sensor assembly 17, in one embodiment, includes an oxygen saturation sensor. In another embodiment, a dual sensor assembly 17 includes an oxygen saturation sensor and a pressure sensor. A lead 14 includes a signal conductor in a configuration which includes only one sensor or two or conductors in a configuration which includes two sensors.

In general, the implantable medical device 21 shown in FIG. 1 includes a hermetically-sealed enclosure which may include various elements, such as an electrochemical cell (e.g., a lithium battery), circuitry that controls device/sensor operations and records sensor data, and a telemetry transceiver antenna and circuit that transmits stored data in a telemetry uplink to an external processing unit, in addition to other components. Implantable medical device 21 may also include a circuit that receives downlinked telemetry commands from an external processing unit.

The medical device 21 is representative of an implantable electrical device capable of obtaining blood oxygen data from a sensor, preferably provided in the right ventricle of a patient's heart, and transmitting this data to a receiving device external to the patient. By way of example, medical device 21 may be an implantable cardiac pacemaker, a pacemaker/cardioverter/defibrillator (PCD), an implantable blood oxygen sensing monitor, or a hemodynamic status monitor. The present invention is believed to find wide application to any form of implantable electrical device which acquires venous oxygen saturation data, in accordance with one embodiment, or, in accordance with another embodiment, acquires blood pressure data in addition to venous oxygen saturation data.

Figure 2:
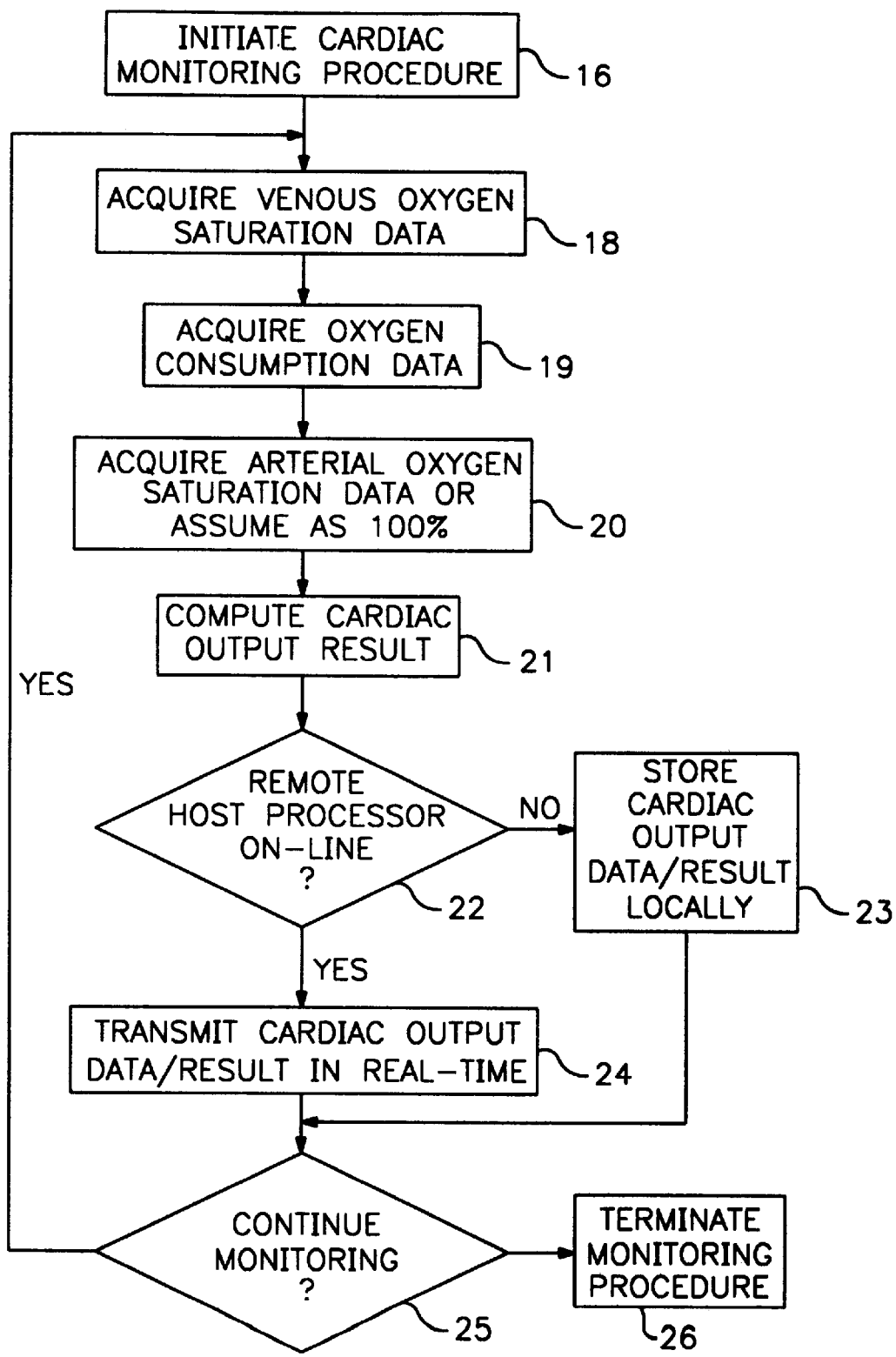
FIG. 2 is a flow diagram depicting various process steps associated with computing cardiac output data in accordance with an embodiment of the present invention.

FIG. 2 is a flow diagram depicting various steps associated with a non-invasive technique for determining a patient's cardiac output in accordance with an embodiment of the present invention. Upon initiating 16 a non-invasive cardiac monitoring procedure, venous oxygen saturation data is acquired 18 through use of a previously implanted blood oxygen monitoring device. Oxygen consumption data is acquired 19 using a breathing apparatus external to the patient. Arterial oxygen saturation data may be assumed 20 as 100% or, alternatively, acquired 20 through use of an external sensor. The patient's cardiac output is computed 21 using the acquired and, if applicable, assumed data. The cardiac output data/result may be stored 23 locally or transmitted 24 to a remote host processor in real-time, assuming the remote host processor is on-line 22. The cardiac monitoring procedure may be continued 25 or terminated 26 as desired.

Figure 3:
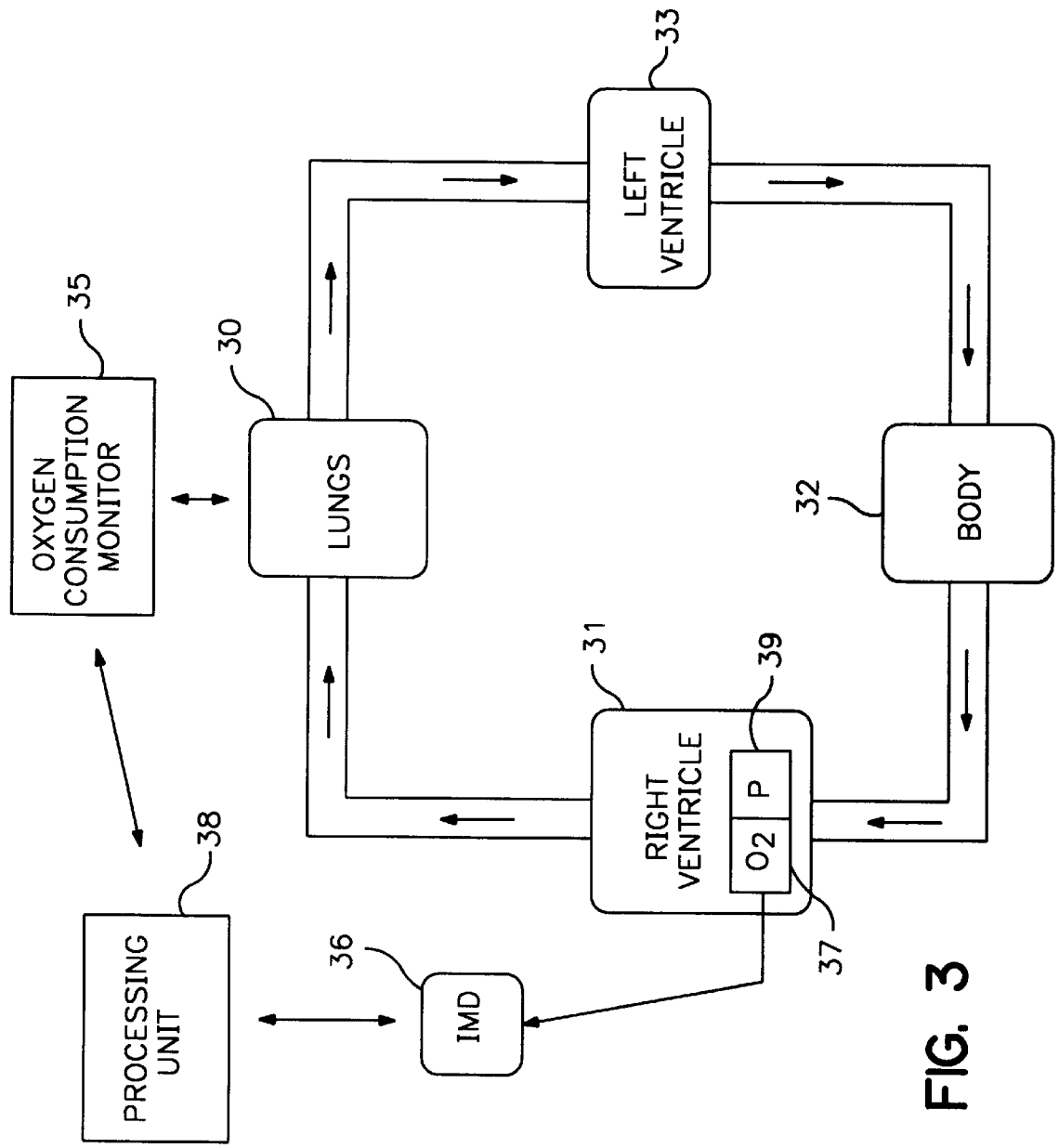
FIG. 3 is a simplified depiction of a patient's pulmonary and systemic systems and a non-invasive cardiac monitoring system for acquiring cardiac output data in real-time in accordance with an embodiment of the present invention.

FIG. 3 is a simplified depiction of a patient's pulmonary and systemic systems including right and left ventricles 31, 33, lungs 30, and body 32. The simplified depiction of FIG. 3 shows the direction of blood flow from the right ventricle 32, through lungs 30, left ventricle 33, body 32, and returning to right ventricle 31. In one embodiment of the present invention, the patient's cardiac output is determined using a non-invasive approach which employs the well-known Fick principle. Using the Fick principle, cardiac output may be calculated as a ratio of oxygen consumption to a difference between arterial and venous oxygen saturation, as is characterized by the following equation:

$$CO = \frac{O_2 \text{ Consumption}}{\text{Arterial } O_2 \text{ Saturation} - \text{Venous } O_2 \text{ Saturation}} \quad [1]$$

where, CO represent the cardiac output result in terms of liters per minute (L/min), $O_2$ consumption is expressed in terms of milliliters per minute (mL/min), and arterial and venous $O_2$ saturation is expressed in terms of milliliters per liter (mL/L).

A patient's oxygen consumption may be measured and determined through use of an oxygen consumption monitor 35. Oxygen consumption monitor 35 measures oxygen consumption using an apparatus through which a patient breathes. The breathing apparatus, in accordance with the one embodiment, includes an instrument which directly measures oxygen consumption. In an alternative embodiment, oxygen consumption monitor 35 includes a breathing apparatus provided with a flow sensor. In accordance with this embodiment, oxygen consumption is computed using the flow sensor in combination with a sensor that senses the oxygen content of ambient air.

Computing a patient's oxygen consumption requires knowing the saturation of expired air and air flow given in terms of volume per unit time. Ambient air is typically 20.93% oxygen. Oxygen consumption may be determined using the following equation:

$$(O_2\text{Sat}_I - O_2\text{Sat}_E) \times \text{Expired Air Flow} \quad [2]$$

where, $O_2$ $\text{Sat}_I$ represents oxygen saturation of inspired air in terms of mL/L, $O_2$ $\text{Sat}_E$ represents oxygen saturation of expired air in terms of mL/L, and Expired Air Flow is given in terms of L/min.

In computing cardiac output, a patient's arterial oxygen may be assumed to be 100% or, alternatively, may be obtained with precision using a sensor external to the patient, such as a pulse oximeter. Venous oxygen saturation is preferably obtained using an oxygen sensor 37 and an implantable medical device (IMD) 36 previously implanted in the patient's right ventricle 31. Venous oxygen saturation data is acquired by oxygen sensor 37 and communicated to IMD 36. The venous oxygen saturation data is communicated from IMD 36 to a processing unit 38 external to the patient. In accordance with one embodiment of the present invention, the processing unit 38 acquires oxygen consumption data while simultaneously acquiring venous oxygen saturation data from IMD 36. In an embodiment in which arterial oxygen saturation is not assumed to be 100%, processing unit 38 acquires arterial oxygen saturation data from the arterial oxygen saturation sensor while simultaneously acquiring oxygen consumption and venous oxygen saturation data. According to this embodiment, the patient's cardiac output is calculated by processing unit 38 in real-time, and may further be transmitted to a remotely located health care facility in real-time via a communications link.

In accordance with an alternative embodiment, venous oxygen saturation data may be acquired using oxygen sensor 37 and communicated from IMD 36 to the external processing unit 38 using various known telemetry techniques. Processing unit 38 obtains oxygen consumption data from oxygen consumption monitor 35 and, if applicable, further obtains arterial oxygen saturation data from an external sensor, such as a pulse oximeter. These data are processed by processing unit 38 to calculate the patient's cardiac output using Equation [1] above. In accordance with this embodiment, the cardiac output data is temporarily stored in processing unit 38 and accumulated over time.

Cardiac output data may be acquired at prescribed times, such as during times of patient activity or inactivity (e.g., during sleep), and stored in processing unit 38. Stored cardiac output data may be transmitted to a remote health care facility on an automatic basis in response to expiration of a predetermined time period, in response to a patient's input command, or in response to the patient's cardiac output falling below a preestablished safety threshold.

In an embodiment in which a preestablished safety threshold has been exceeded, processing unit 38 may transmit an emergency communication to the health care facility followed by transmission of the patient's cardiac output data. Processing unit 38 may further be programmed to automatically transmit an alert message to an emergency response operator (e.g., 911 operator) or facility, such as a local fire/paramedic station. Alternatively, a remote host processor may poll the processing unit 38 via a communication link and obtain a patient's cardiac output data stored in processing unit 38 or acquire same in real-time. It is understood that a remote host processor may communicate with a number of distantly located cardiac monitoring systems of the present invention.

Figure 4:
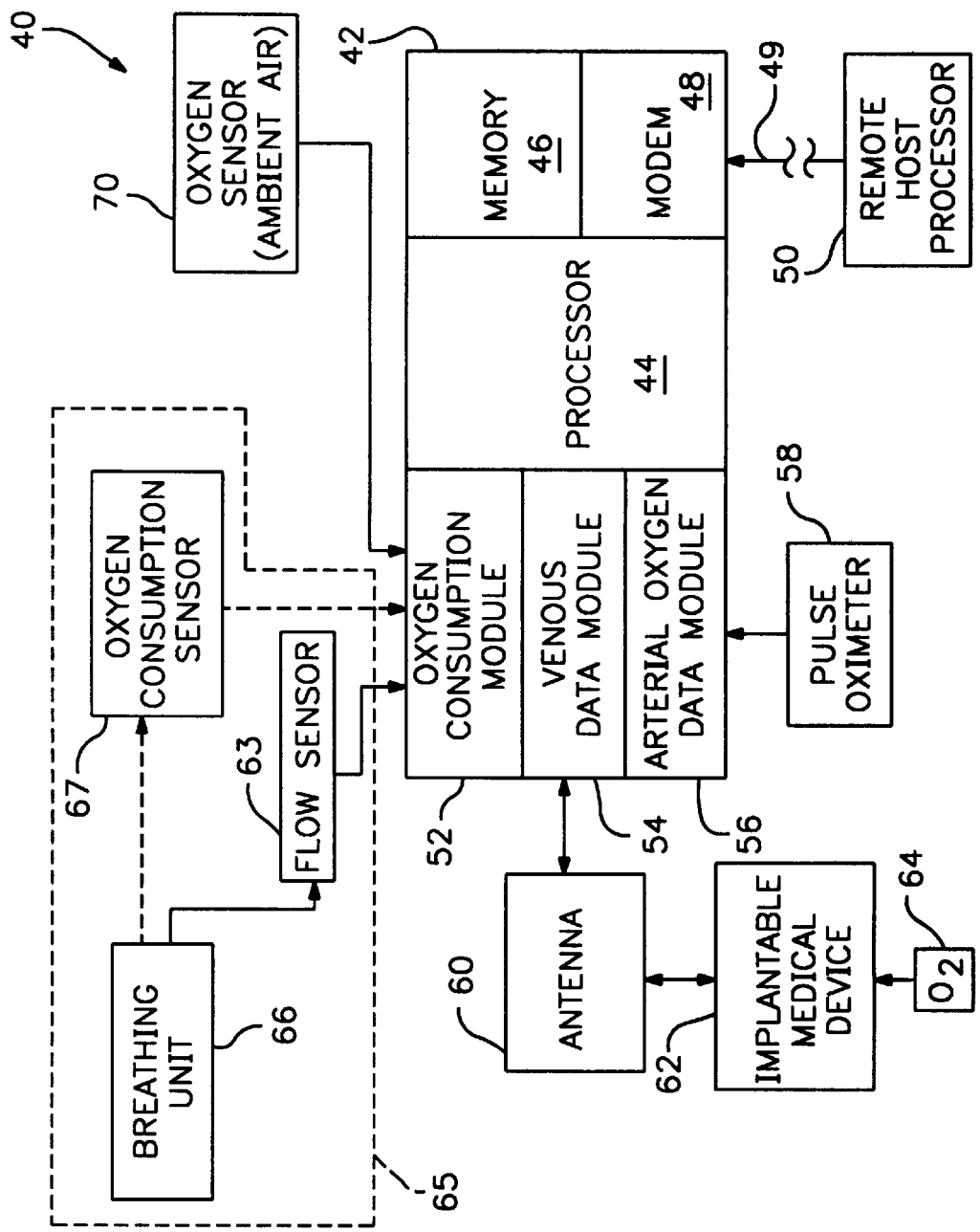
FIG. 4 is a block diagram of a non-invasive cardiac monitoring system for acquiring cardiac output data at a patient's home and for communicating such data to a remote host processor via a communications link in accordance with an embodiment of the present invention.

Referring now to FIG. 4, a cardiac output monitoring system 40 includes a processing unit 42. Processing unit 42 includes a main processor 44, such as a microprocessor, coupled to a memory 46. Also coupled to processor 44 are oxygen consumption module 52, venous oxygen data module 54, and arterial oxygen data module 56. It is understood that modules 52, 54, and 56 represent data processing units or devices which may be separate from or integral to processor 44. By way of example, the functionality implemented by modules 52, 54, and 56 may be performed within a single integrated processing circuit with appropriate input/output interfaces provided for receiving information signals from one or more external sensors or sources. Alternatively, the functionality associated with modules 52, 54, and 56 may be implemented using discrete processing devices, each of which may communicate with processor 44 via an appropriate interface or communications bus.

In accordance with the embodiment illustrated in FIG. 4, cardiac output monitoring system 42 acquires venous oxygen saturation data from an oxygen sensor 64 implanted in the right ventricle of a patient's heart. An exemplary oxygen saturation sensor 64 well suited for use in the various embodiments described herein is described in U.S. Pat. Nos. 4,750,495 and 4,903,701, both of which are issued to Moore, et al., and incorporated herein by reference in their respective entireties. Oxygen sensor 64 is coupled to an implantable medical device 62 implanted in the patient's body. In one embodiment, venous oxygen saturation data sensed by oxygen sensor 64 and acquired by IMD 62 is transmitted to cardiac output monitoring system 42 through use of an antenna 60. Oxygen saturation data is transmitted from IMD 62 in the form of electromagnetic signals, such as radio frequency (RF) encoded signals, out of the patient's body, and received by antenna 60. Antenna 60 may be incorporated as part of the programmer head of an external programming unit, such as the programmer head of commercially available Medtronic Model 9790 Programmer.

Communication of oxygen saturation telemetry data through use of electromagnetic signals may be accomplished in a manner disclosed in U.S. Pat. No. 4,556,063 issued to Thompson, et al., or in U.S. Pat. No. 5,312,453 issued to Wyborny, et al., both of which are incorporated herein by reference in their respective entireties. The venous oxygen saturation telemetry data received via antenna 60 is processed by venous oxygen data module 54 to produce a numerical value suitable for use in Equation [1] above.

In accordance with another embodiment, venous oxygen saturation data acquired by IMD 62 is transmitted in the form of acoustic signals using a piezoelectric crystal or other acoustic signal source provided within IMD 62 as is known in the art. In such a configuration, antenna 60 would be replaced with a suitable acoustic receiving device, such as a microphone. The acoustic signals may then be transmitted to venous oxygen data module 54 in either analog or digital form. Communication of oxygen saturation telemetry data through use of acoustic signals may be accomplished in a manner disclosed in U.S. Pat. No. 5,113,859 to Funke, the content of which is incorporated by reference herein in its entirety.

As previously mentioned, the arterial oxygen saturation term of equation [1] above may be assumed to be 100%. Alternatively, it may be desirable to provide a more precise value of arterial oxygen saturation when calculating a patient's cardiac output, such as by using the Fick principle characterized in Equation [1] above. In this case, processing unit 42 may include an arterial oxygen data module 56 which is coupled to a pulse oximeter 58. As will be appreciated by those skilled in the art, a pulse oximeter 58 represents a sensor which is typically affixed to a patient's finger for purposes of providing arterial oxygen saturation. Arterial oxygen data module 56 computes the arterial oxygen saturation level from signals received from pulse oximeter 58. It will be understood that arterial oxygen data module 56 need not be a component of processing unit 42 if arterial oxygen saturation is assumed to be 100% in the cardiac output calculation.

Oxygen consumption module 52 is coupled to a breathing apparatus 65 which provides oxygen consumption data to processing unit 42. Breathing apparatus 65 includes a breathing unit 66 through which the patient breathes. In one embodiment, an oxygen consumption sensor 67 directly measures the patient's oxygen consumption and provides an information signal to oxygen consumption module 52 indicative of oxygen consumption. A suitable oxygen consumption sensor 67 is commercially available from Medical Graphics Corporation or Beckman Instruments.

In accordance with another embodiment, breathing unit 66 is coupled to a flow sensor 63 which measures air flow passing through the sensor 63. Air flow data is transmitted from flow sensor 63 to oxygen consumption module 52. In accordance with this embodiment, an oxygen sensor 70 is used to determine the content of oxygen in the ambient air, and oxygen sensor 67 senses the content of oxygen in the patient's expired air. Alternatively, the content of oxygen in ambient air may be assumed to be 20.93%. Oxygen consumption module 52 uses the air flow data acquired from flow sensor 63, oxygen content data received from oxygen sensor 67, and assumed (i.e., 20.93%) or sensed oxygen content data (i.e., via ambient oxygen sensor 70) to compute oxygen consumption of the patient in real-time. By way of example, oxygen consumption module 52 may compute a patient's oxygen consumption using Equation [2] provided above.

An important aspect of the embodiment illustrated in FIG. 4 concerns the transmission of cardiac output data acquired by processing unit 42 to a remote host processor 50 via modem 48. In accordance with this embodiment, processing unit 42 acquires, in real-time, oxygen consumption data, arterial and venous oxygen saturation data, and computes cardiac output data for communication to the remote host processor 50 in real-time via modem 48. Alternatively, cardiac output data acquired and computed by processor 44 of processing unit 42 may be stored in memory 46 for subsequent transmission to the remote host processor 50.

It is noted that modem 48 of processing unit 42 may communicate with remote host processor 50 using various communication channels and technologies, including analog and digital telephone lines, high speed ISDN and T-1/2/3 lines, cable lines, optical fiber lines, satellite links, microwave links, public or private networks, the Internet, and the like. The remote host processor 50 is typically provided at, or accessible to, a health care center or clinic which may monitor real-time or non-real-time cardiac output data for a particular patient. Cardiac output data may be obtained from the patient on a continuous basis, periodic basis, as-needed basis, at the request of a physician communicating with the remote host processor 50 from a local access site (e.g., physician's office) or a remote access site (e.g., from home), or at the patient's request.

Figure 5:
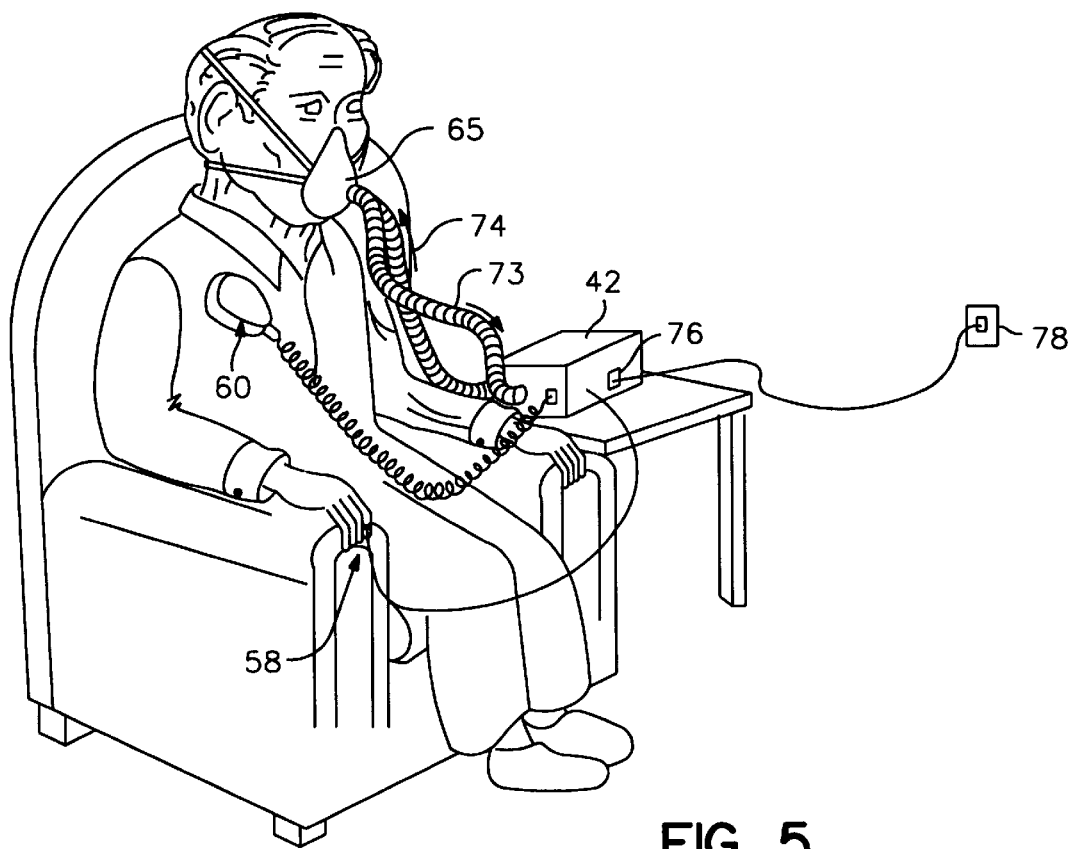
FIG. 5 is an illustration of a non-invasive cardiac monitoring system as employed by a patient in the home in accordance with an embodiment of the present invention.

FIG. 5 is an embodiment of a cardiac monitoring system configured for home use. In FIG. 5, a patient is shown sitting comfortably in a chair with a breathing apparatus 65 placed over the mouth and nose. Breathing tubes 73, 74 respectively direct air exhaled by the patient to the oxygen consumption module 52 of the processing unit 42 and direct fresh air from the processing unit 42 or an ambient source to the breathing apparatus 65. The flow sensor 63 and/or oxygen consumption sensor 67 may be situated within the processing unit 42 forming part of the oxygen consumption module 52 or, alternatively, be situated proximate the mask of breathing apparatus 65 or within breathing tube 73.

A programmer head or other antenna device 60 is shown affixed to the patient's clothing proximate the heart area of the chest and connected to the venous oxygen data module 54 of the processing unit 42 via an extendable conductor. It will be appreciated that the criticality of positioning the antenna device 60 relative to the heart area varies depending on the telemetry approach employed. Certain telemetry techniques are considered position sensitive in that such techniques require relatively small separation distances between the antenna device 60 and the implanted medical device. Other telemetry techniques are considered position insensitive in that greater antenna-to-implantable medical device separation distances may be tolerated. A radio frequency (RF) telemetry technique, for example, may allow for antenna-to-implantable medical device separation distances on the order of several feet.

In a configuration in which arterial oxygen saturation is not assumed to be 100%, a pulse oximeter 58 may be secured to the patient's finger and coupled to the arterial oxygen data module 56 of the processing unit 42 through use of an appropriate conductor. Modem 48 of processing unit 42 is connected to an appropriate communications interface 78 at the home for establishing a communication link between the processing unit 42 and a remote host processor 50.

Communications interface 76 may represent a standard analog or digital telephone jack, cable line interface, satellite system interface, fiber optic line interface, or the like. Alternatively, communications interface 76 may be representative of an input/output interface of a personal computer (PC). The PC may be used to store cardiac output data acquired by processing unit 42. The stored cardiac output data may be subsequently or contemporaneously transmitted to the remote host processor 50 via the PC's modem. In this configuration, it will be appreciated that enhanced cardiac output computations, historical data analysis, charting, and displaying capabilities may be provided through appropriate software running on the PC. In this manner, a set of enhanced features for acquiring, processing, and interfacing with processing unit 42 and the remote host processor 50 is made available through use of a PC or other computing system provided at the patient's home.

Figure 6:
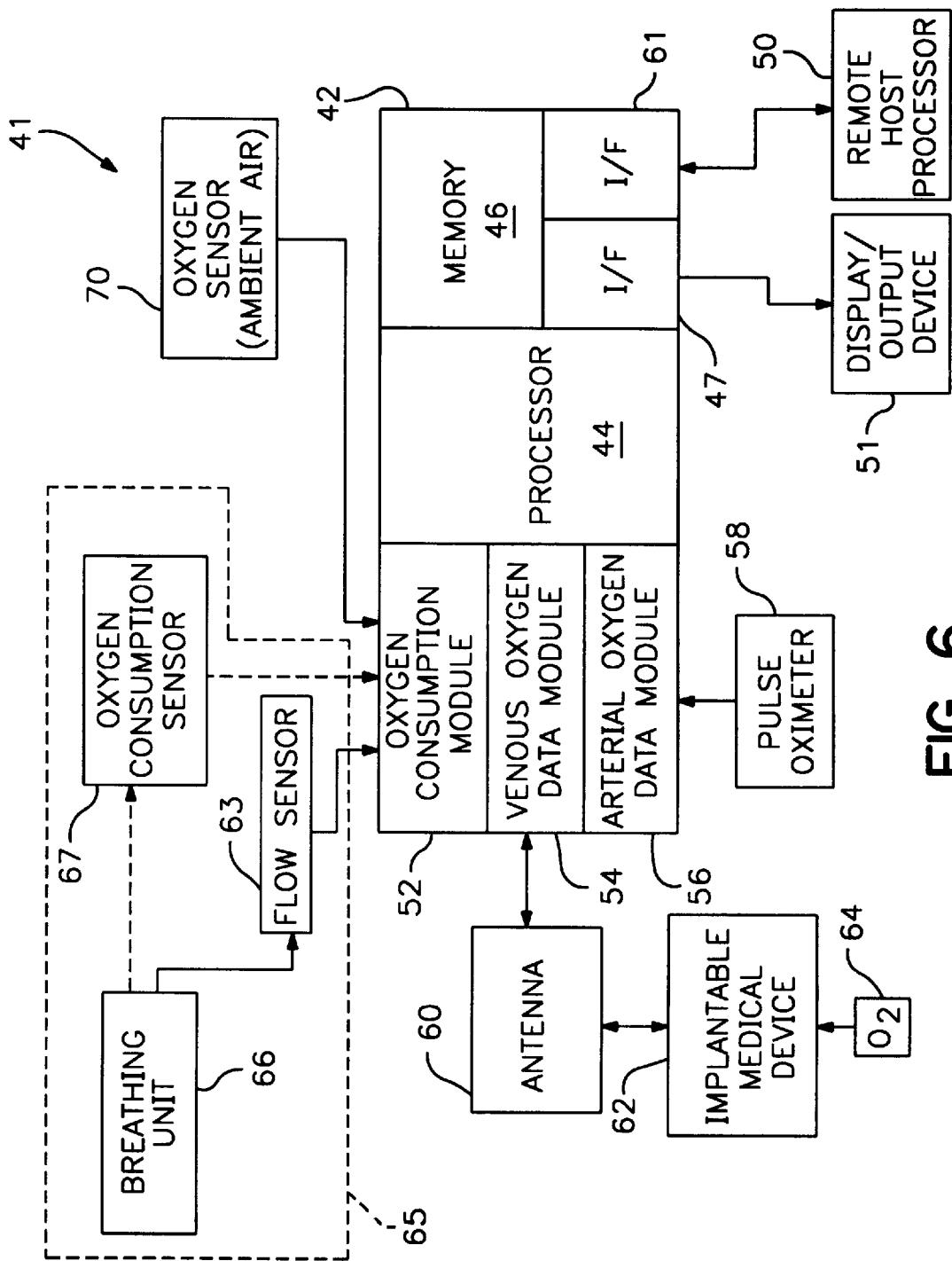
FIG. 6 is a block diagram of a non-invasive cardiac monitoring system for acquiring cardiac output data at a physician's office or a health care clinic, for producing cardiac output data, and for communicating such data to a local display/output device and/or a remote host processor.

Referring now to FIG. 6, there is illustrated an alternative embodiment of a cardiac monitoring system 41 which includes many of the components previously described with respect to the embodiment of FIGS. 4 and 5. The embodiment shown in FIG. 6 is configured for use in a physician's office or other health care clinic location. As such, the cardiac monitoring system 41 typically does not include a modem 48 for communicating with a remote host processor 50. Rather, the embodiment of FIG. 6 includes an input/output interface 47 for communicating cardiac output data from processing unit 42 to a display or other output device 51. Processing unit 42 may also include a communications interface 61 for communicating with a local host processor 50, such as through a local area network connection. It is noted that communications interface 61 need not be included in this configuration if transmission of cardiac output data to a remote host processor or network connection is not desired.

The embodiment of a cardiac monitoring system 41 depicted in FIG. 6 is believed particularly useful for determining, in an efficient and non-invasive manner, the cardiac output of a patient who is visiting a physician's office or a health care clinic. In particular, cardiac output data for a particular patient may be ascertained within minutes after the patient arrives at the physician's office or health care clinic. Obtaining cardiac output information in accordance with the principles of the present invention wholly obviates the need for drawing blood samples from the patient and awaiting return of cardiac output results from laboratory evaluation of the blood samples, which may represent a delay of several hours or days.

Figure 7:
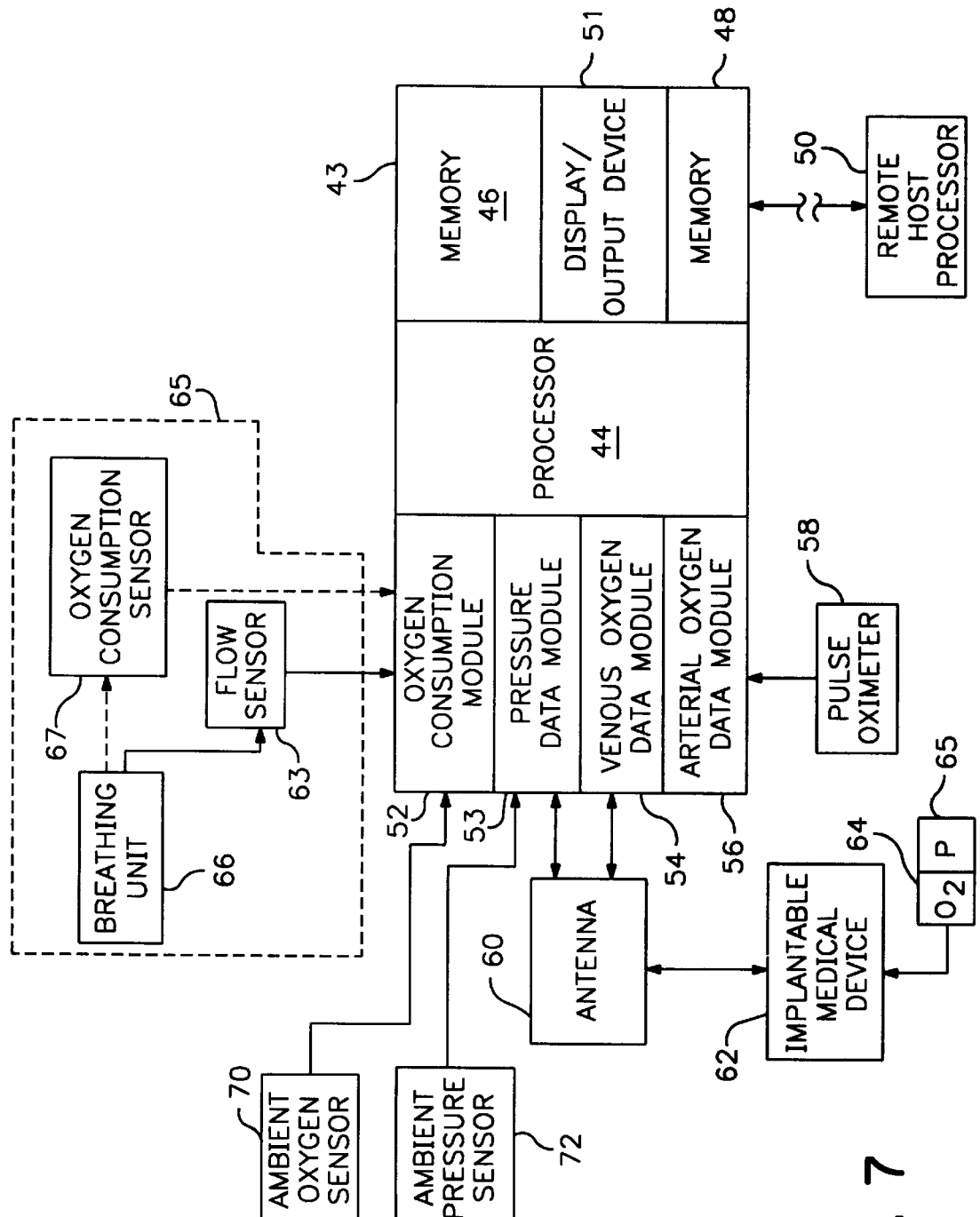
FIG. 7 is a block diagram of a non-invasive hemodynamic status monitoring system for acquiring oxygen saturation and pressure data at either a patient's home or a physician's office or health care clinic and for communicating such data to a local display/output device and/or a remote host processor.

FIG. 7 illustrates another embodiment of the present invention which includes all or some of the cardiac output data acquisition and computation capabilities previously discussed. In addition, the system embodiment shown in FIG. 7 provides for the acquisition of blood pressure and ambient air pressure data which, when combined with cardiac output data, provides for the hemodynamic status of the patient. In accordance with this embodiment, the implantable medical device 62 is coupled to an oxygen sensor 64 and a pressure sensor 65, both of which are provided in the right ventricle of the patient's heart. Oxygen and pressure data acquired from sensors 64, 65 are received by IMD 62 and uplinked to processing unit 46 via antenna 60.

An exemplary capacitive absolute pressure sensor well suited for use in the system configuration depicted in FIG. 7 is described in U.S. Pat. Nos. 5,535,752 and 5,564,434, both of which are issued to Halperin, et al., and incorporated herein by reference in their respective entireties. It is noted that the capacitive absolute pressure sensors disclosed in U.S. Pat. Nos. 5,535,752 and 5,564,434 each represent a single sensor that monitors two distinct physiologic parameters; namely, an absolute blood pressure parameter and a blood temperature parameter. An exemplary dual oxygen saturation/pressure sensor which may also be used in the system embodiment illustrated in FIG. 7 is disclosed in U.S. Ser. No. 09/182,970 (Miesel et al.), filed Oct. 30, 1998, and entitled "MULTIPLE SENSOR ASSEMBLY FOR MEDICAL ELECTRICAL LEAD," the content of which is incorporated herein by reference it its entirety.

In accordance with another embodiment of the present invention, the ambient pressure sensor 72 is integrated into the programmer head in which antenna 60 is provided, such as programmer head 60 shown in FIG. 5. A pressure data module 53 provided in the processing unit 43 receives ambient pressure data from the ambient pressure sensor 72. Pressure data obtained from pressure sensor 65 by IMD 62 is transmitted via antenna 60 to pressure data module 53. The patient's blood pressure data is then computed by pressure data module 53. It is noted that pressure data module 53 typically uses calibration data or curves generated during manufacture of the pressure sensor lead, and further subtracts the value of ambient barometric air pressure, when computing a patient's blood pressure.

Processing unit 43 computes the hemodynamic status of a patient using this and other data acquired by processing unit 43. The system embodiment depicted in FIG. 7 may be used to provide for non-invasive real-time hemodynamic status monitoring of a patient at either a home location, a physician's office or a health care clinic location.

The system depicted in FIG. 7 may be configured to include a display/output device 51 exclusive of, or in addition to, a modem 48. The display/output device 51 may be integrated as part of the processing unit 43 or may constitute a display or output device 51 separate from the processing unit 43. Processing unit 43 may further include a communications interface for communicating with a host processor or other computing system resource via a local area or wide area network.

Figure 8:
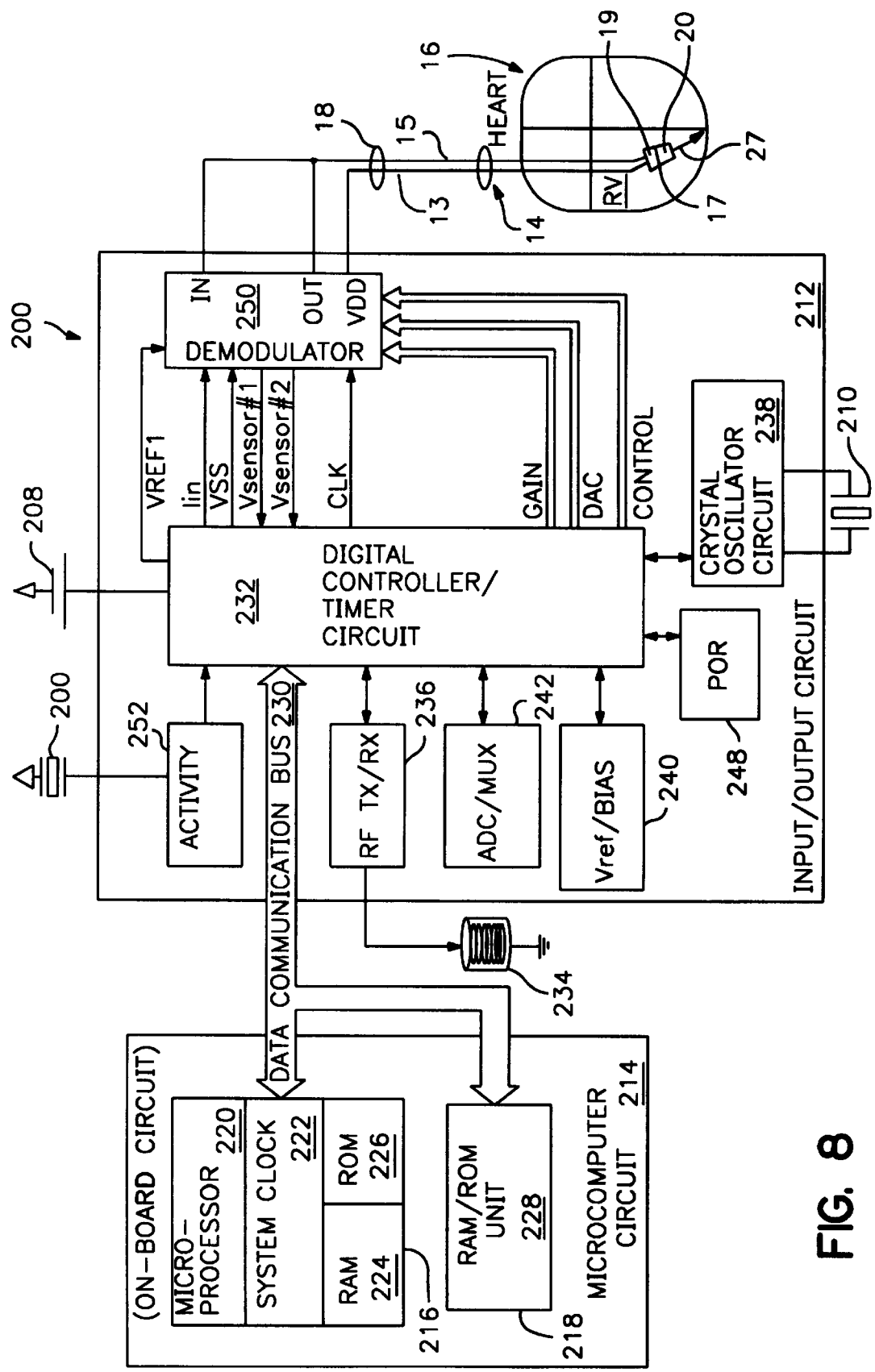
FIG. 8 is a block diagram of an implantable pacemaker device which may be coupled to one or more physiologic sensors and adapted for acquiring oxygen saturation data, exclusive of or in addition to pressure data, and for communicating such data to an external cardiac monitoring system in accordance with an embodiment of the present invention.

FIG. 8 is a functional schematic diagram from U.S. Pat. No. 5,342,406 to Thompson illustrating an implantable cardiac pacemaker which represents one of many implantable medical devices which may be adapted to derive physiologic information for producing cardiac output data and/or hemodynamic status data using a non-invasive approach in accordance with the present invention. U.S. Pat. No. 5,342,406 is incorporated by reference herein in its entirety. It is understood that this diagram is an illustration of an exemplary type of implantable pacemaker device in which the invention may find application, and is not intended to limit the scope of the present invention. For example, the present invention is also believed to be useful in conjunction with implantable pacemakers as disclosed in U.S. Pat. Nos. 5,158,078 and 5,154,170 to Bennett et al., U.S. Pat. No. 5,312,453 to Shelton et al., or U.S. Pat. No. 5,144,949 to Olson, all hereby incorporated herein by reference in their respective entireties.

Figure 9:
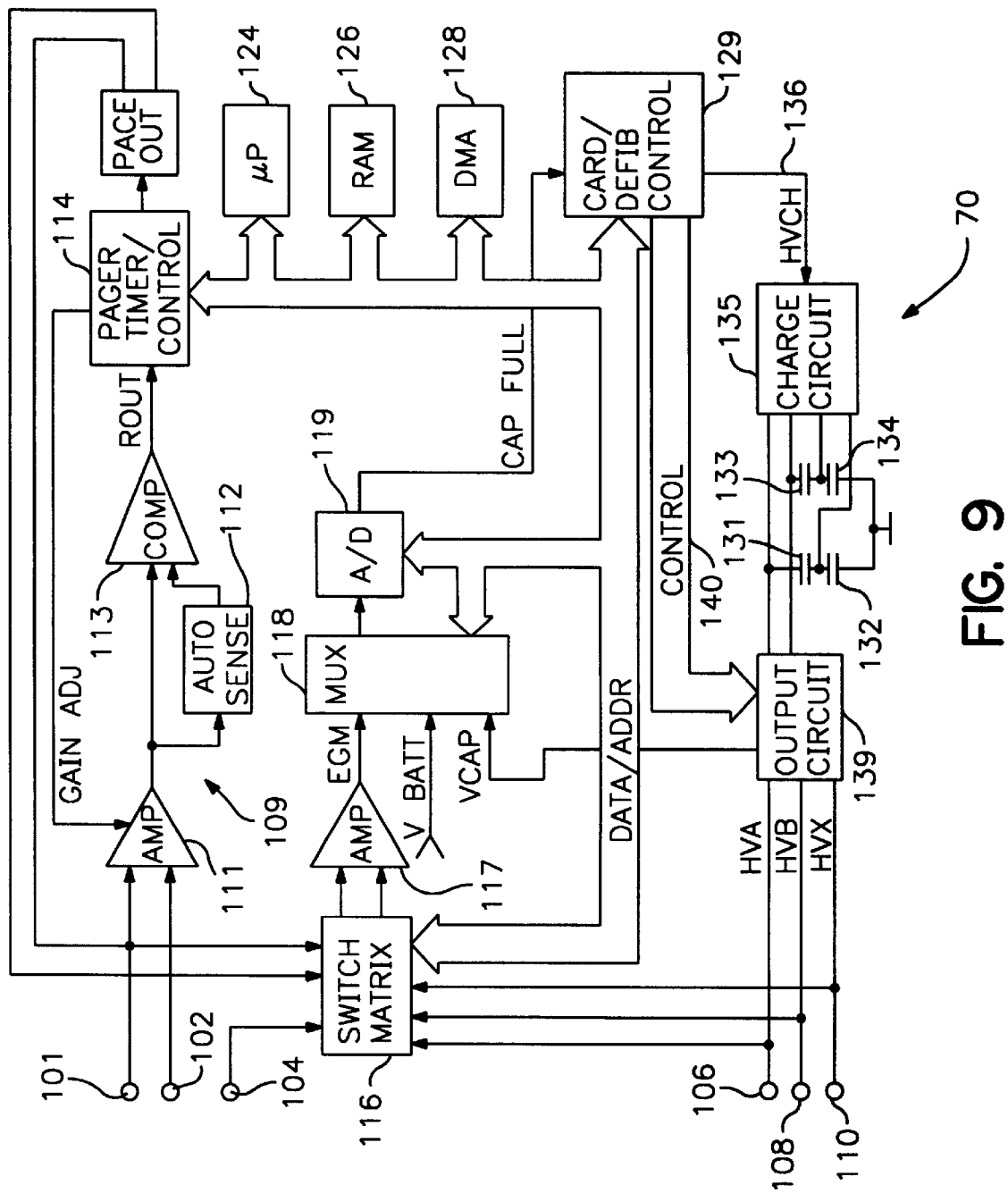
FIG. 9 is a block diagram of a pacemaker/cardioverter/defibrillator unit which may be coupled to one or more physiologic sensors and adapted for acquiring oxygen saturation data, exclusive of or in addition to pressure data, and for communicating such data to an external cardiac monitoring system in accordance with an embodiment of the present invention.

FIG. 9 is a functional schematic diagram from U.S. Pat. No. 5,447,519 to Peterson illustrating an implantable pacemaker/cardioverter/defibrillator (PCD) which represents another one of many implantable medical devices which may be adapted to derive physiologic information for producing cardiac output data and/or hemodynamic status data using a non-invasive approach in accordance with the present invention. U.S. Pat. No. 5,447,519 is incorporated by reference herein in its entirety. The present invention is also believed to be useful in conjunction with implantable PCD devices as disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, or U.S. Pat. No. 4,821,723 to Baker et al., U.S. Pat. No. 4,548,209 to Wielders, et al.; U.S. Pat. No. 4,693,253 to Adams et al.; U.S. Pat. No. 4,830,006 to Haluska et al.; and U.S. Pat. No. 4,949,730 to Pless et al., all hereby incorporated herein by reference in their respective entireties. Other implantable medical devices having functional organizations wherein the present invention may be useful may also be modified in accordance with the principles of the present invention.

The foregoing description of the various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A non-invasive cardiac monitoring apparatus, comprising:
    an implantable medical device coupled to an oxygen sensor, the oxygen sensor providing venous oxygen saturation data to the implantable medical device;
    an oxygen consumption unit, the oxygen consumption unit producing oxygen consumption data using air exhaled by a patient; and
    a processing unit that receives the venous oxygen saturation data from the implantable medical device and the oxygen consumption data from the oxygen consumption unit, the processing unit calculating a cardiac output result using the venous oxygen saturation data, the oxygen consumption data, and arterial oxygen saturation data, the cardiac output result provided at an output of the processing unit.

2. The apparatus of claim 1, wherein the arterial oxygen saturation data is assumed to be about 100% or is acquired using a sensor external to the patient.

3. The apparatus of claim 2, wherein the sensor comprises a pulse oximeter.

4. The apparatus of claim 1, wherein the processing unit receives the venous oxygen saturation data from the implantable medical device and the oxygen consumption data from the oxygen consumption unit substantially simultaneously.

5. The apparatus of claim 1, wherein the processing unit calculates the cardiac output result substantially in real-time.

6. The apparatus of claim 1, wherein the oxygen consumption unit comprises a mask, securable about the patient's nose and mouth, and a sensor assembly, the sensor assembly measuring one or more oxygen consumption parameters.

7. The apparatus of claim 6, wherein the sensor assembly comprises an oxygen consumption sensor.

8. The apparatus of claim 1, wherein the oxygen consumption unit comprises a mask, securable about the patient's nose and mouth, a flow sensor, and an oxygen sensor for measuring oxygen content of ambient air, the mask directing the exhaled air through the flow sensor.

9. The apparatus of claim 8, wherein the processing unit computes an oxygen consumption value using oxygen content of ambient air and flow rate data corresponding to a flow rate of the exhaled air measured by the flow sensor.

10. The apparatus of claim 1, wherein the processing unit computes the cardiac output result using Fick's principle.

11. The apparatus of claim 1, wherein the cardiac output result, CO, computed by the processing unit is characterized by:

$$CO = \frac{O_2 \text{ Consumption}}{\text{Arterial } O_2 \text{ Saturation} - \text{Venous } O_2 \text{ Saturation}}.$$

12. The apparatus of claim 1, further comprising:
    an implantable pressure sensor coupled to the implantable medical device; and
    an air pressure sensor external to the patient and coupled to the processing unit, the processing unit receiving blood and ambient air pressure data from the implantable pressure sensor and air pressure sensor, respectively, and calculating hemodynamic data using the venous oxygen saturation data, oxygen consumption data, arterial oxygen saturation data, and the blood and ambient air pressure data.

13. The apparatus of claim 1, wherein the implantable medical device comprises one of a pacemaker, a pacemaker/cardioverter/defibrillator (PCD), an oxygen sensing device, or an implantable hemodynamic monitor.

14. The apparatus of claim 1, wherein the implantable medical device transmits the venous oxygen saturation data to the processing unit using electromagnetic signals or acoustic signals.

15. A non-invasive cardiac monitoring apparatus, comprising:
    an implantable medical device coupled to an oxygen sensor, the oxygen sensor providing venous oxygen saturation data to the implantable medical device;
    an oxygen consumption unit, the oxygen consumption unit producing oxygen consumption data using air exhaled by a patient;
    a processing unit that calculates a cardiac output result using the venous oxygen saturation data, the oxygen consumption data, and arterial oxygen saturation data assumed to be about 100% or acquired using a sensor external to the patient; and
    an interface, the processing unit communicating the cardiac output result to a remote host processor or to a local output device via the interface.

16. The apparatus of claim 15, wherein the interface comprises a modem, a computer interface, a network interface, or a communications system interface.

17. The apparatus of claim 15, wherein the local output device comprises a display, a charting device, or a printing device.

18. The apparatus of claim 15, wherein the processing unit receives the venous oxygen saturation data from the implantable medical device and the oxygen consumption data from the oxygen consumption unit substantially simultaneously, and the processing unit calculates the cardiac output result substantially in real-time.

19. The apparatus of claim 18, wherein the processing unit stores the cardiac output result or communicates the cardiac output result to the remote host processor substantially in real-time.

20. The apparatus of claim 15, wherein either the processing unit or the remote host processor initiates communication of the cardiac output result to the remote host processor or to the local output device.

21. The apparatus of claim 15, wherein the processing unit communicates the cardiac output result to the remote host processor in an analog, digital or optical form.

22. The apparatus of claim 15, wherein the oxygen consumption unit comprises a mask, securable about the patient's nose and mouth, and a sensor assembly, the sensor assembly measuring (1) a flow rate of exhaled air and oxygen content in ambient air or (2) oxygen consumption.

23. The apparatus of claim 15, wherein the processing unit computes the cardiac output result using Fick's principle.

24. The apparatus of claim 15, wherein the implantable medical device transmits the venous oxygen saturation data to the processing unit using electromagnetic signals or acoustic signals.

25. The apparatus of claim 15, wherein the implantable medical device comprises one of a pacemaker, a pacemaker/cardioverter/defibrillator (PCD), an oxygen sensing device, or an implantable hemodynamic monitor.

26. A non-invasive cardiac monitoring method, comprising:

receiving venous oxygen saturation data from an implantable medical device coupled to an oxygen sensor;

receiving oxygen consumption data using air exhaled by a patient;

and calculating a cardiac output result using the venous oxygen saturation data, the oxygen consumption data, and arterial oxygen saturation data assumed to be about 100% or acquired using a sensor external to the patient.

27. The method of claim 26, wherein the oxygen consumption data is obtained by measuring (1) a flow rate of air exhaled by the patient and oxygen content in ambient air or (2) the patient's oxygen consumption.

28. The method of claim 26, wherein the cardiac output result is calculated using Fick's principle.

29. The method of claim 26, wherein the venous oxygen saturation data is received substantially simultaneously with respect to the oxygen consumption data.

30. The method of claim 26, wherein the cardiac output result is calculated substantially in real-time.

31. The method of claim 26, further comprising communicating the cardiac output result to a remote host processor or to a local output device.

32. The method of claim 26, further comprising communicating the cardiac output result to a remote host processor in response to an instruction signal produced by the remote host processor.

33. The method of claim 26, further comprising communicating the cardiac output result to a remote host processor in response to the cardiac output result exceeding a preestablished threshold.

34. The method of claim 26, wherein the implantable medical device comprises one of a pacemaker, a pacemaker/cardioverter/defibrillator (PCD), an oxygen sensing device, or an implantable hemodynamic monitor.

35. The method of claim 26, further comprising:

acquiring blood pressure data and ambient air pressure data from the implantable pressure sensor and an air pressure sensor, respectively; and calculating hemodynamic data using the venous oxygen saturation data, oxygen consumption data, arterial oxygen saturation data, and the blood and ambient air pressure data.

* * * * *